United States Patent [19]
Baszczynski et al.

[11] Patent Number: 5,767,379
[45] Date of Patent: Jun. 16, 1998

[54] COMMERCIAL PRODUCTION OF AVIDIN IN PLANTS

[75] Inventors: Chris Baszczynski, Urbandale; Elizabeth Hood, Clive; Sheila Maddock, Johnston; Terry EuClaire Meyer, Urbandale; James C. Register, III, Ames; Derrick Witcher, Urbandale; John A. Howard, Wes Des Moines, all of Iowa

[73] Assignee: John Howard, Des Moines, Iowa

[21] Appl. No.: 554,586

[22] Filed: Nov. 6, 1995

[51] Int. Cl.$^6$ ............... C12N 15/12; C12N 15/29; C12N 15/82; A01H 5/00
[52] U.S. Cl. .................... 800/205; 800/DIG. 56; 800/250; 435/69.1; 435/240.4; 435/320.1; 435/172.3; 435/69.8; 536/235; 536/24.1; 536/23.6
[58] Field of Search ............... 800/205, DIG. 56, 800/250; 435/69.1, 240.4, 172.3, 320.1, 69.8; 536/24.1, 23.5, 23.6

[56] References Cited

U.S. PATENT DOCUMENTS

| | | | |
|---|---|---|---|
| 4,914,025 | 4/1990 | Manoil et al. | 435/69.8 |
| 4,956,282 | 9/1990 | Goodman et al. | 435/69.51 |
| 5,460,952 | 10/1995 | Yu et al. | 435/69.1 |

FOREIGN PATENT DOCUMENTS

| | | |
|---|---|---|
| WO 86 02077 | 4/1986 | WIPO. |
| WO 90/01551 | 2/1990 | WIPO. |
| WO 92/01370 | 2/1992 | WIPO. |
| WO 94/00992 | 1/1994 | WIPO. |
| WO 95/14099 | 5/1995 | WIPO. |
| WO 96/40949 | 12/1996 | WIPO. |

OTHER PUBLICATIONS

DeLange et al., "Egg White Avidin". Sequence of the 78-Residue Middle Cyanogen Peptide. Complete Amino Acid Sequence of the Protein Subunit, J. of Boil. Chem., vol. 246, No. 3, pp. 698–709, (1971).

Keinanen et al., "Molecular Cloning and Nucleotide Sequence of Chicken Avidin–Related Genes 1–5", Eur. J. Biochem., vol. 220, pp. 615–621, (1994).

Van Der Hoeven et al., "Variability of Organ–Specific Gene Expression in Transgenic Tobacco Plants", Transgenic Research, vol. 3, pp. 159–165, (1994).

Morgan et al. Entomologia Experimentalis et Applicata vol. 69 No. 2 97–108 Avidin and Streptavidia as Insecticidal and Growth Inhibiting . . . , 1993.

Keinanen et al. J. Steroid Biochem. vol. 30 No. 1–6 17–21, 1988 Molecular Cloning of Three Structurally . . . .

Gordon–Kamm et al. The Plant Cell, vol. 2 603–618 Jul. 1990 Transformation of Maize Cells and Regeneration of Fertile . . . .

Cornejo et al. Plant Molecular Biology 23 567–581 1993 Activity of Maize Ubiquitin Promoter in Transgenic Rice.

Guan et al. "Expression of streptavidin gene in tobacco and its effects on bacteria", Plant Physiol. 102(1) May 1993 Abstract #XP 002017747.

Hood et al. "Commercial production of avidin from transgenic maize", In Vitro. World Congress In Vitro Biology May 21–25, 1995 Abstract #P1002.

Kulomaa et al. "Production of recombinant avidin and avidin–fusion proteins . . . ", Annual Meeting of Am. Society for Biochemistry, May 21–25 (1995), Abst. #802.

Airenne et al. "Production of recombinant avidin in Eschericia coli", Gene 144: 75–80 (1994).

During et al. Synthesis and self–assembly of a functional monoclonal antibody in transgenic Nicotiana tabacum, Plant Mol. Biol. 15: 281–293 (1990).

Goodjin et al., "Plants as Bioreactors", Trands in Biotechnology 13(9): 379–387 (1995).

Primary Examiner—David T. Fox
Assistant Examiner—Thomas Haas
Attorney, Agent, or Firm—Foley & Lardner

[57] ABSTRACT

A method for commercial production of avidin entails heterologous expression of the protein in plants, in native conformation, at an expression level such that avidin represents at least 0.1% of total extracted protein. A genetic map of the integration locus allows for the identification of the avidin-expressing plant. Genetic loci on a plant chromosome are revealed that support high levels of avidin expression and that can be used as a site of integration for high level expression of other genes of interest.

12 Claims, 1 Drawing Sheet

FIG. 1A

```
  1 GGATCCCAAC AATGGCCAAC AAGCACCTGA GCCTCTCCCT CTTCCTCGTG
 51 CTCCTCGGCC TCTCCGCCTC CCTCGCCAGC GGCGCCAGGA AGTGCTCCCT
101 CACCGGCAAG TGGACCAATG ACCTCGGCTC CAACATGACC ATCGGCGCCG
151 TGAACTCCAG GGGCGAGTTC ACCGGCACCT ACATCACCGC CGTGACCGCC
201 ACCTCCAACG AGATCAAGGA GTCCCCCCTC CACGGTACCC AGAACACCAT
251 CAACAAGAGG ACCCAGCCCA CCTTCGGCTT CACCGTGAAC TGGAAGTTCT
301 CCGAGTCCAC CACCGTGTTC ACCGGCCAGT GCTTCATCGA CCGCAACGGC
351 AAGGAGGTGC TCAAGACCAT GTGGCTCCTG AGGAGCTCCG TGAATGACAT
401 CGGCGACGAC TGGAAGGCCA CCCGCGTGGG CATCAACATC TTCACCCGCC
451 TCCGCACCCA GAAGGAGTGA TAGTTAACGA ATTC
```

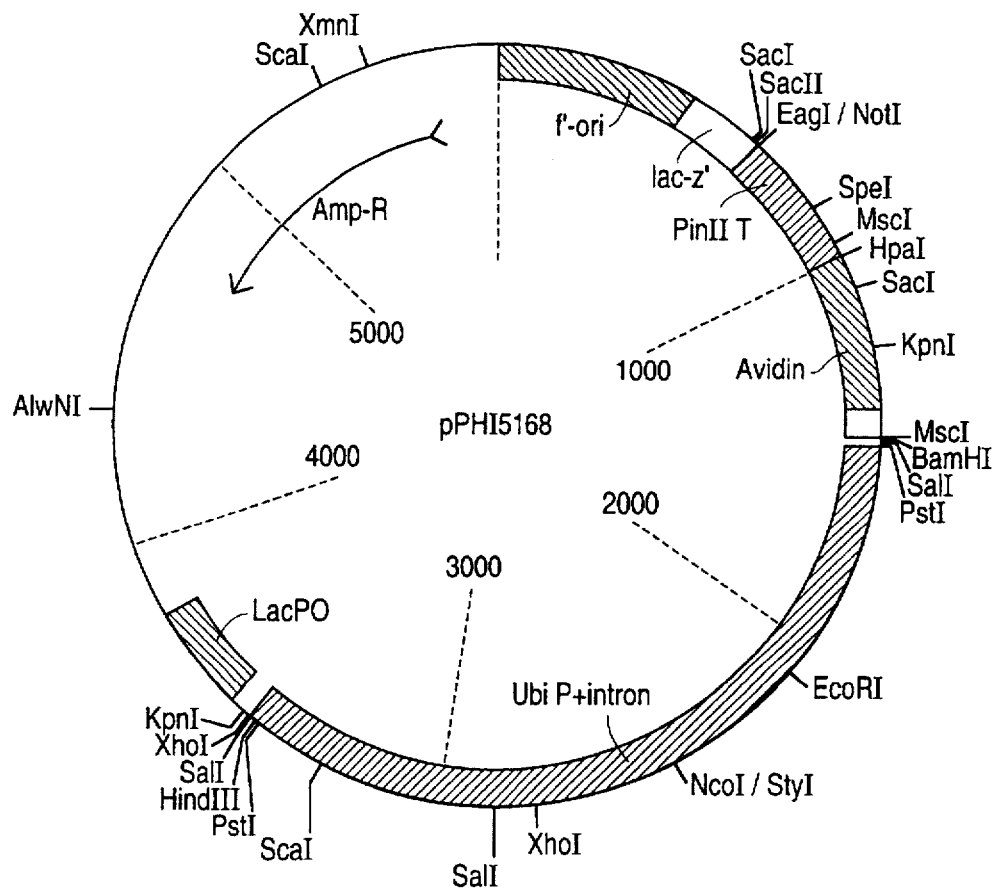

FIG. 1B

COMMERCIAL PRODUCTION OF AVIDIN IN PLANTS

BACKGROUND OF THE INVENTION

Avidin is a glycoprotein found in avian, reptilian and amphibian egg white. Its gene expression is induced by progesterone as well as by certain events, such as tissue trauma, the presence of toxic agents, and bacterial and viral infections. Induction appears to be primarily at the transcription level. The protein avidin is composed of four identical subunits, each 128 amino acids long. The amino acid sequence has been known since 1971. DeLange and Huang, *J. Biol. Chem.* 246: 698–709 (1971). The cDNA of the chicken avidin gene was documented by Gope et al., *Nucleic Acid Res.* 15: 3595–06 (1987), and the genomic clone by Keinanen et al., *J. Steroid Biochem.* 30: 17–21 (1988). More recently, Keinanen et al., *European J. Biochem.* 220: 615–21 (1994), identified a family of closely related avidin genes.

Avidin forms a particularly strong, non-covalent bond with biotin. It is this property of avidin that is responsible for its commercial value, since it allows for detection of proteins and nucleic acids molecules incorporating biotin. The customary source for commercial production of avidin has been chicken egg white, a method of relatively high production costs.

Expression of foreign genes in plants is amply documented. In general, the expression of the foreign gene has been desired to benefit the plant, for example, by the action of expressed antifungals or growth factors; to improve an agronomic trait, such as fruit ripening or nutritional content; or to induce sterility in the context of creating hybrid plants. It also is feasible to express in plants heterologous genes, expressing high value products. In many cases, expression in plants could be the system of choice, because of such inherent advantages such as cost relative to that of tissue culture, and the concern about correct glycosylation and other post-translational processing of the expression product from other expression systems.

The level of protein expression in plants can be influenced by many factors. One factor is the choice of transcriptional promoters used. Recently, the range of available plant compatible promoters has increased to include tissue-specific and inducible promoters. Some of the better documented constitutive promoters include the CaMV 35S promoter and tandem arrangements of this promoter, and the ubiquitin promoter. See Kay et al., *Science* 236: 1299 (1987), and European patent application No. 0 342 926. Yet other factors that can be manipulated to control levels of expression are the presence of transcriptional modification factors such as introns, polyadenylation and transcription termination sites. At the translational level, other factors to consider are the ribosomal binding site and the codon bias of the gene. High level expression of a gene product which then accumulates in the cytoplasm may result in toxicity to the plant cell; removal of the gene product from the cytoplasm thus may result in overall higher expression levels. Plant genes and their export signal sequences are known. See Jones and Robinson, Tansley Review, 17, pp. 567–597 (1989). Furthermore, intron sequences within the avidin gene also may increase its expression level by stabilizing the transcript and allowing its effective translocation from the nucleus. Many plant genes contain intron sequences. For example, see Callis et al., Genes and Development, 1: 1183–1200 (1987) and Cornejo et al., Plant Mol. Biol. 23: 567–518, (1993). Among the known such intron sequences are the introns of the plant ubiquitin gene, Cornejo et al., Id. It also has been observed that the same construct inserted at different loci on the genome can vary in the level of expression in plants. The effect is believed to be due at least in part to the position of the gene on the chromosome, i.e., individual isolates will have different expression levels. See, for example, Hoever et al., *Transgenic Res.* 3: 159–66 (1994) (report regarding constructs containing gus or nptII). Yet another consideration in expression of foreign genes in plants is the level of stability of the transgenic genome, i.e., the tendency of a foreign gene to segregate from the population. If a selective marker is linked to the gene of interest, then selection can be applied to maintain the transgenic plant.

SUMMARY OF THE INVENTION

It therefore is an object of the present invention to provide an approach to the commercial production of avidin which yields protein in native conformation at a substantial savings over conventional methodology.

It also is an object of the present invention to allow for tracking of unauthorized propagation of a plant by reference to a genetic map of the region where a heterozygotic avidin gene has been introduced.

It is a further object of the present invention to provide an approach to the cloning of a gene for high-level, heterologous expression, based on integration of the gene at a position analogous to that of an avidin gene in a high-expressing, transgenic plant.

In accomplishing these and other objectives, there has been provided, in accordance with one aspect of the present invention, a DNA molecule that comprises (i) a plant-compatible promoter and (ii) a heterologous avidin-encoding sequence that is operably linked to said promoter. In a preferred embodiment, the avidin-encoding sequence incorporates plant-preferred codons. In another preferred embodiment, the DNA molecule described above that is comprised of a plant-compatible promoter and a heterologous avidin-encoding sequence, further comprises an intron sequence or a peptide export signal sequence which modifies expression of the avidin-encoding sequence. In a further preferred embodiment, the peptide export signal sequence is a barley alpha amylase peptide export signal sequence. In a yet further preferred embodiment, the intron sequence is a plant ubiquitin intron sequence.

In accordance with a second aspect of the present invention, a transgenic plant is provided that contains a DNA molecule as described above. In a preferred embodiment, the transgenic plant is a corn plant. In another preferred embodiment, from the transgenic plant, at least 0.1% of total extracted protein is avidin. In a further preferred embodiment, the transgenic plant provided is of strain 70415, germplasm of which strain has been deposited under ATCC Accession No. 97328.

In accordance with a third aspect of the present invention, a method of producing avidin in commercial quantities is provided, comprising the steps of (i) providing biomass from a plurality of plants, of which at least certain plants contain a DNA molecule comprised of a heterologous nucleotide sequence coding for avidin, wherein said nucleotide sequence is operably linked to a promoter to effect expression of avidin by said certain plants; and (ii) extracting avidin from said biomass. In a preferred embodiment the biomass from which avidin is extracted is comprised of seeds.

In accordance with a fourth aspect of the present invention, a method of determining whether a first transgenic plant of unknown parentage is derived from a second transgenic plant is provided, comprising the steps of:

(a) making a genetic map of the integration region of the nucleotide sequence coding for avidin in the second transgenic plant;

(b) making a genetic map of tie integration region of said nucleotide sequence coding for avidin in said first transgenic plant; and then (c) comparing the maps of steps (a) and (b) to ascertain whether the insertion sites are the same.

In accordance with a fifth aspect of the present invention, a method of expressing genes at high levels in a plant is provided, comprising the steps of:

(a) cloning from a transgenic plant that expresses high levels of avidin a chromosomal fragment comprising a heterologous DNA sequence coding for avidin;

(b) cloning a chromosomal fragment corresponding to the chromosomal fragment of step (a) from a plant that does not express heterologous avidin;

(c) constructing an expression vector comprising the chromosomal fragment isolated in step (b);

(d) preparing a construct of a gene desired to be expressed at high levels within the vector, wherein the gene is located within the plant chromosomal fragment of the vector of step (c) at a position corresponding to the heterologous avidin gene;

(e) transforming the constructs in plant cells or tissue;

(f) propagating plants from the transformed cells or tissue; and (g) based on an assessment of expression level for the gene desired to be expressed at high levels, selecting at least one plant for further propagation to produce the gene product.

Other objects, features and advantages of the present invention will become apparent from the following detailed description. It should be understood, however, that the detailed description and the specific examples, while indicating embodiments of the invention, are given by way of illustration only, since various changes and modifications within the spirit and scope of the invention will become apparent to those skilled in the art from this detailed description.

BRIEF DESCRIPTION OF THE DRAWING

FIG. 1A. A nucleotide sequence of the BamHI/EcoRI fragment is shown (SEQ. I.D. NO: 1) which contains the barley alpha amylase signal sequence fused to the avidin mature protein sequence, such that normal cellular processing will accurately cleave the molecule to yield mature active avidin. The synthesis and assembly of this sequence are described below, for example, in Example 1. Restriction enzyme sites for BamHI, HpaI and EcoRI are built-in and are unique and, hence, available for further cloning. They are underlined, italicized, and underlined plus italicized, respectively. The initiator ATG codon of the barley alpha amylase leader sequence and the TGA translation termination codon of the avidin gene are shown in bold.

FIG. 1B. A restriction map of pPHI5168 is depicted. pPHI5168 is a transformation vector in which a maize ubiquitin promoter (including its first exon plus first intron) drives expression of a barley alpha amylase export signal sequence and an avidin coding region, followed by a PinII transcription termination sequence.

DETAILED DESCRIPTION OF THE PREFERRED EMBODIMENTS

The present inventors have determined that commercial production of avidin in plants not only is feasible but also offers substantial advantages over the conventional approach of obtaining the protein from chicken egg white. The raw materials for plant-based production are cheaper and more stable, which reduces storage expenses, and the cost of extracting avidin is diminished, since volume of biomass that must be subjected to extraction is reduced. It has been discovered, moreover, that heterologous expression of avidin in plants can yield protein in native conformation, at levels accommodating commercial needs.

In accordance with the present invention, therefore, a DNA molecule comprising a transformation/expression vector is engineered to incorporate avidin-encoding DNA. Extant knowledge concerning the respective sequences for five chicken avidin genes permits the isolation and cloning, by standard methodology, of a suitable avidin gene from chicken. Another approach to the cloning of an avidin gene, especially from related species, would employ a functional assay based on the binding of avidin to biotin, the analysis of the isolated avidin, and its "reverse engineering" to reveal the putative nucleic acid sequence. For either approach, the methodologies used would include identification of the gene by hybridization with probes, PCR, probe/primer/synthetic gene synthesis, sequencing, molecular cloning and other techniques which are well-known to those skilled in molecular biology. In a preferred embodiment, the avidin gene employed in the invention encodes the avidin protein found in chicken egg white. In a further preferred embodiment, the gene is synthesized to reflect preferred codon usage in plants. Murray et al., Nucleic Acid Res. 17: 477–498 (1989).

In yet another preferred embodiment, the expression level of avidin is increased by providing the genetic construct containing the avidin gene with a sequence that codes for a peptide export signal sequence. See Jones and Robinson, supra. The construct is made such that a signal peptide is fused to the N-terminal of the mature avidin protein sequence, allowing for normal cellular processing to cleave accurately the protein molecule and yield mature active avidin. In a particularly preferred embodiment, signal sequence is the barley alpha amylase signal sequence. Rogers, J. Biol. Chem. 260: 3731–3738 (1985).

In a still further preferred embodiment the expression levels of avidin are increased by providing the genetic construct containing t avidin gene with an intron sequence. Plant intron sequences are associated with many plant genes. See for example Callis et al., supra and Cornejo et al., supra. In a particularly preferred embodiment, the intron sequence added to the avidin gene corresponds to the sequence of the first exon and first intron of a plant ubiquitin gene.

The methods available for putting together such a relatively short, synthetic gene which further may comprise various modifications for enhancing the expression level, as described above (intron, peptide export signal sequence, codon usage), can differ in detail. But the methods in question generally include the designing and synthesis of overlapping, complementary synthetic oligonucleotides which are annealed and ligated together to yield a gene with convenient restriction sites for cloning. These are all standard techniques for a molecular biologist.

Once an avidin gene has been isolated and engineered to contain some or all features described above, it is placed into an expression vector by standard methods. The selection of an appropriate expression vector will depend upon the method of introducing the expression vector into host cells. A typical expression vector contains: prokaryotic DNA elements coding for a bacterial replication origin and an antibiotic resistance gene to provide for the growth and selection of the expression vector in the bacterial host; a cloning site for insertion of an exogenous DNA sequence, which in this context would code for avidin; eukaryotic DNA elements that control initiation of transcription of the exogenous gene, such as a promoter; and DNA elements that control the processing of transcripts, such as a transcription termination/polyadenylation sequence. It also could contain such sequences as necessary to allow for the eventual integration of the vector into the chromosome.

In a preferred embodiment, the expression vector also contains a gene encoding a selection marker which is functionally linked to promoters that control transcription initiation. For a general description of plant expression vectors and reporter genes, see Gruber et al., "Vectors for Plant Transformation," in METHODS IN PLANT MOLECULAR BIOLOGY AND BIOTECHNOLOGY 89-119 (CRC Press, 1993).

A promoter element employed to control expression of avidin and the reporter gene, respectively, can be any plant-compatible promoter. Those can be plant gene promoters, such as, for example, the promoter for the small subunit of ribulose-1,5-bis-phosphate carboxylase, or promoters from tumor inducing plasmid *Agrobacterium tumefaciens*, such as the nopaline synthase and octopine synthase promoters, or viral promoters such as the cauliflower mosaic virus (CaMV) 19S and 35S promoters or the figwort mosaic virus 35S promoter. See international application WO 91/19806 for a review of illustrative plant promoters suitably employed in the present invention.

In a preferred embodiment, the promoter that controls expression of avidin is "tissue-preferred," in the sense that the avidin expression driven by the promoter is particularly high in the tissue from which extraction of the protein is desired; some expression may occur in other parts of the plant. Examples of known tissue-preferred promoters include the tuber-directed class I patatin promoter, Bevan et al., *Nucleic Acids Res.* 14: 4625-38 (1986); the promoters associated with potato tuber ADPGPP genes, Muller et al., *Mol. Gen. Genet.* 224: 136-46 (1990); the soybean promoter of β-conglycinin, also known as the 7S protein, which drives seed-directed transcription, Bray, *Planta* 172: 364-370 (1987); and seed-directed promoters from the zein genes of maize endosperm, Pedersen et al., *Cell* 29: 1015-26 (1982).

In another preferred embodiment of the present invention, the exogenous, avidin-encoding DNA is under the transcriptional control of a plant ubiquitin promoter. Plant ubiquitin promoters are well known in the art, as evidenced by European patent application No. 0 342 926. In another preferred embodiment, the selective gene is bar under the transcriptional control of the CaMV 35S promoter. In this construct, transcriptional activity is enhanced by a DNA fragment representing part of the CaMV 35S promoter being placed in a direct repeat tandem arrangement with the CaMV 35S promoter. See Kay et al. (1987), supra. The bar gene confers resistance to bialophos and to tabtoxin-β-lactam toxins. See Gordon-Kamm et al., *The Plant Cell* 2: 603 (1990); Uchimiya et al., *Bio/Technology* 11: 835 (1993), and Anzai et al., *Mol. Gen.* 219: 492 (1989).

In yet another preferred embodiment, separate expression vectors are constructed which contain an avidin gene under the control of a plant ubiquitin promoter and the bar gene under the control of the CaMV 35S tandem promoter, respectively. In another preferred embodiment, both the avidin and the bar gene, along with their transcriptional control elements, are located on one DNA molecule.

In accordance with the present invention, a transgenic plant is produced that contains a DNA molecule, comprised of elements as described above, integrated into its genome so that the plant expresses a heterologous, avidin-encoding DNA sequence. In order to create such a transgenic plant, the expression vectors containing an avidin gene can be introduced into protoplasts; into intact tissues, such as immature embryos and meristems; into callus cultures or into isolated cells. Preferably, expression vectors are introduced into intact tissues. General methods of culturing plant tissues are provided, for example, by Miki et al., "Procedures for Introducing Foreign DNA into Plants," in METHODS IN PLANT MOLECULAR BIOLOGY AND BIOTECHNOLOGY, Glick et al. (eds.), pages 67-88 (CRC Press 1993), and by Phillips et al., "Cell/Tissue Culture and In Vitro Manipulation," in CORN AND CORN IMPROVEMENT, 3rd Edition, Sprague et al. (eds.), pages 345-387 (American Society of Agronomy 1988). The reporter gene incorporated in the DNA molecule allows for selection of transformants.

Methods for introducing expression vectors into plant tissue include the direct infection or co-cultivation of plant tissue with *Agrobacterium tumefaciens*, as described, for example, by Horsch et al., *Science* 227: 1229 (1985). Preferably, a disarmed Ti-plasmid is used as a vector for foreign DNA sequences. Transformation can be performed using procedures described, for example, in European applications No. 0 116 718 and No. 0 270 822.

Other types of vectors can be used for transforming plant cells by procedures such as direct gene transfer, as described, for example, in PCT application WO 8501856 and in European application No. 0 275 069; in vitro protoplast transformation, which is the subject of U.S. Pat. No. 4,684,611, for instance; plant virus-mediated transformation, illustrated in European application No. 0 67 553 and U.S. Pat. No. 4,407,956; and liposome-mediated transformation according to U.S. Pat. No. 4,536,475, among other disclosures. Standard methods for the transformation of rice are described by Christou et al., *Trends in Biotechnology* 10: 239 (1992), and by Lee et al., *Proc. Nat'l Acad. Sci. USA* 88: 6389 (1991). Wheat can be transformed by techniques similar to those employed for transforming corn or rice. Furthermore, Casas et al., supra, describe a method for transforming sorghum, while Wan et al., *Plant Physiol.* 104: 37 (1994), describe a method for transforming barley. In a preferred embodiment, the transgenic plant of the present invention is maize. Suitable methods for corn transformation are provided by Fromm et al., *Bio/Technology* 8: 833 (1990), and by Gordon-Kamm et al., supra.

In general, direct transfer methods are preferred for the transformation of a monocotyledonous plant, particularly a cereal such as rice, corn, sorghum, barley or wheat. Suitable direct transfer methods include microprojectile-mediated delivery, DNA injection, electroporation, and the like. See, for example, Gruber et al., "Vectors for Plant Transformation," in METHODS IN PLANT MOLECULAR BIOLOGY AND BIOTECHNOLOGY, Miki et al., "Procedures for Introducing Foreign DNA into Plants," in METHODS IN PLANT MOLECULAR BIOLOGY AND BIOTECHNOLOGY, and Klein et al., *Bio/Technology* 10: 268 (1992).

Seed from strain 70415, a plant transformed with vectors comprising elements according to the present invention, has been deposited with the American Type Culture Collection (ATCC) in Rockville, Md., under Accession No. 97328. The vectors in question are designated pPHI5168 and pPHI610. The former vector comprises the ubiquitin promoter, including the first exon and intron; the barley alpha amylase export signal sequence; an avidin-encoding sequence modified to reflect plant-preferred codon usage; and PinII as a transcription termination sequence. The other vector, pPHI610, comprises a CaMV tandem promoter operably linked to the bar gene.

The present inventors have observed that heterologous avidin gene expression in plants leads to male sterility. For the purposes of propagating such plants, and for generating seed according to the present invention, a method of overcoming male sterility is required.

There are numerous options for overcoming male sterility induced by avidin. One approach for the propagation of a male-sterile line would cultivate the male sterile plant in close physical proximity with a male fertile plant, where the two plants may otherwise be isogenic. But the commonly proposed approach to restoring fertility in a line of transgenic male-sterile plants requires the production of a second "restorer" line of transgenic plants.

For example, a restorer line of transgenic plants would express ribozymes targeted to avidin mRNA or would express antisense avidin. Ribozymes can be designed to express endonuclease activity that is directed to a certain target sequence in a mRNA molecule. For example, Steinecke et al., *EMBO J.* 11: 1525 (1992), achieved up to 100% inhibition of neomycin phosphotransferase gene expression by ribozymes in tobacco protoplasts. More recently, Perriman et al., *Antisense Res. & Devel.* 3: 253 (1993), inhibited chloramphenicol acetyl transferase activity in tobacco protoplasts using a vector that expressed a modified hammerhead ribozyme. In the context of the present invention, avidin MRNA provides the appropriate target RNA molecule for ribozymes.

In a similar approach, fertility can be restored by the use of an expression vector containing a nucleotide sequence that encodes an antisense RNA. The binding of antisense RNA molecules to target mRNA molecules results in hybridization-mediated arrest of translation. Paterson et al., *Proc. Nat'l Acad. Sci. USA* 74: 4370 (1987). In the context of the present invention, a suitable antisense RNA molecule would have a sequence that is complementary to avidin mRNA. The antisense RNA would be under the control of an inducible promoter. Activation of this promoter then allows restoration of male fertility.

In another approach, the avidin expression inhibiting gene of the restorer line encodes RNA transcripts capable of promoting RNase P-mediated cleavage of avidin mRNA molecules. By this approach an external guide sequence can be constructed for directing the endogenous ribozyme, RNase P, to avidin mRNA, which is subsequently cleaved by the cellular ribozyme. See U.S. Pat. No. 5,168,053 and Yuan et al., *Science* 263: 1269 (1994). Preferably, the external guide sequence comprises a ten to fifteen nucleotide sequence complementary to avidin mRNA, and a 3'-NCCA nucleotide sequence, wherein N is preferably a purine. Id. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region. Id.

In an alternative method for restoring male fertility, the transgenic, male-sterile restorer plants express a prokaryotic transcription-regulating polypeptide. In the F1 hybrids, the prokaryotic polypeptide binds to a prokaryotic regulatory sequence upstream of avidin gene and represses the expression of avidin. For example, the expression vector of the male-sterile plant would contain the LexA operator sequence, while the expression vector of the male-fertile plant would contain the coding sequences of the LexA repressor. See U.S. Pat. No. 4,833,080 and Wang et al., *Mol. Cell. Biol.* 13: 1805 (1993). In the F1 hybrid, the LexA repressor would bind to the LexA operator sequence and inhibit transcription of the avidin gene. Those of skill in the art can readily devise other male fertility restoration strategies using prokaryotic regulatory systems, such as the lac repressor/lac operon system, or the trp repressor/trp operon system, or bacteriophage T7 promoters and T7 RNA polymerase gene.

Still another method for restoring fertility utilizes the high affinity of avidin for biotin. By spraying developing plants with a solution of biotin, the effects of avidin could be eliminated by the formation of the avidin-biotin complex. The biotin solution also comprises a minimum amount of an organic solvent such as DMSO to ensure complete solubility of the biotin. Spraying is commenced during the meiotic phase of pollen development, and is repeated at regular intervals until pollen shed is observed.

Among the available restorer systems, some are more desirable and/or currently in use by the inventors. Thus, the avidin male sterile plants of the present invention were propagated by planting a row of avidin plants adjacent to a row of male fertile plants. The male fertile plants cross-pollinated onto the male sterile avidin plants. The seed was collected and used either to grind up and extract protein or saved and used for future growing of avidin plants. The new generation of avidin plants theoretically will be a 50/50 mixture of both sterile plants that have the gene, as well as completely fertile plants which do not. In the next generation, the plants that have sterility problems are considered as the avidin-positive plants. Alternatively, the transformation marker described can also serve as a selection marker in plants. In the presence of a herbicide resistance marker, the plants are sprayed with herbicide. Only those plants that carry the gene are resistant and survive. The cycle then would repeat in future generations. In each cycle, 50% of the plants would not carry the herbicide resistance gene and, hence, would not survive when sprayed with herbicide. In a preferred embodiment, the herbicide resistance is bar, and the toxin is glyphosinate. In another preferred embodiment, the plants are sprayed with biotin over the time period when male structures develop.

Optimizing the level of avidin expression is a preferred course of action in implementing the present invention. To this end, it is useful to ascertain those constructs, transformed plant cells, and transgenic plants, respectively, that are associated with different levels of avidin expression. Two assays suitable for determining expression levels in this regard are an enzymatic assay and an ELISA assay which employs antibody raised against biotin to quantify avidin expression levels.

An ELISA used for quantitative determination of avidin levels can be a double antibody sandwich assay, which utilizes polyclonal goat antibodies obtained commercially. The antibody is conjugated to alkaline phosphatase for detection. The avidin standard also can be obtained commercially. A suitable enzymatic binding assay is described by Green, *Methods Enzymol.* 18A: 418 (1970).

The levels of expression of the gene of interest can be enhanced by the stable maintenance of an avidin gene on a chromosome of the transgenic plant. Use of linked genes, with herbicide resistance in physical proximity to the avidin gene, would allow for maintaining selective pressure on the transgenic plant population and for those plants where the genes of interest are not lost.

With transgenic plants according to the present invention, avidin can be produced in commercial quantities. Thus, the selection and propagation techniques described above yield a plurality of transgenic plants which are harvested in a conventional manner, and avidin then is extracted from a tissue of interest or from total biomass. Avidin extraction from biomass can be accomplished by known methods which are discussed, for example, by Heney and Orr, *Anal. Biochem.* 114: 92–96 (1981).

It should be evident that there are loses of material expected in any extraction methodology. There also are costs of the procedure to be considered. Accordingly, a minimum level of expression of avidin is required for the process to be deemed economically worthwhile. The terms "commercial" and "commercial quantities" here denote a level of expression where at least 0.1% of the total extracted protein is avidin. Higher levels of avidin expression would make this undertaking yet more desirable.

According to a preferred embodiment, the transgenic plant provided for commercial production of avidin is maize. In another preferred embodiment, the biomass of interest is seed.

For example, transgenic corn plants were prepared according to the present invention, seed was harvested, and avidin was extracted from the seed. Table 1 details the results of purifying avidin from the harvested corn seed. As indicated, only about 9% of the extracted protein represented breakdown product and impurities. The extracted avidin maintained an activity of 12.7 U/mg, where a unit (U) is defined as 1 µg of biotin-binding activity.

Table 2 shows data demonstrating a similarity in the biochemical characteristics of the corn-derived avidin versus commercially available avidin, a product of Sigma Chemical Company (St. Louis, Mo.). The molecular weight was determined by gel electrophoresis, on 4–20% SDS-polyacrylamide gels prepared by Novex (San Diego, Calif.). Avidin from the two sources was run in parallel with protein molecular weight standards from Novex. The binding stoichiometry for avidin from the two sources was determined by the biotin binding assay as described by Green, supra. Determination of the isoelectric point for both proteins was performed on a Pharmacia Phastsystem, a product of Pharmacia (Piscataway, N.J.). General methods of determining the isoelectric point of proteins are provided by Walker, "Isoelectric focusing of proteins in ultra-thin polyacrylamide gels," in 32 METHODS IN MOLECULAR BIOLOGY 59–65 (Humana Press 1994). Avidin from both sources was also determined to be antigenically identical by immunodiffusion assay on ouchterlony plates purchased from ICN Biomedicals (Costa Mesa, Calif.). See, Bailey, "The Raising of a Polyclonal Antiserum to a Protein," in 32 METHODS IN MOLECULAR BIOLOGY 383–88 (Humana Press 1994). Furthermore, avidin from both sources was determined to be glycosylated by peroxidase conjugated lectin binding assays. See Ervasti et al., *Cell* 66: 1121–31 (1991).

Table 3 shows results of a partial, N-terminal sequencing of the two proteins (SEQ ID NOS: 2–3, respectively). General methods for N-terminal sequencing of proteins are provided by Charbonneau, "Strategies for obtaining partial amino acid sequence data from small quantities of pure or partially purified protein," in A PRACTICAL GUIDE TO PROTEIN AND PEPTIDE PURIFICATION FOR MICROSEQUENCING 15–30 (Academic Press 1989).

It is apparent from the above-discussed data that avidin from corn seed of transgenic plants within the present invention can be produced at high level, over 1%, of avidin per total extracted protein. Furthermore, avidin extended from maize is structurally and functionally indistinguishable from avidin extracted from chicken egg white.

For the relatively small number of transgenic plants that show higher levels of expression, a genetic map can be generated, primarily via conventional RFLP and PCR analysis, which identifies the approximate chromosomal location of the integrated DNA molecule. For exemplary methodologies in this regard, see Glick and Thompson, in METHODS IN PLANT MOLECULAR BIOLOGY AND BIOTECHNOLOGY 269–84 (CRC Press 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR and sequencing, all of which are conventional techniques.

As discussed above, the location on the chromosome of an integrated, avidin-encoding DNA sequence can explain variation in the level of avidin expression obtainable with plants produced according to the present invention. Genetic mapping can be effected, first to identify DNA fragments which contain the integrated DNA and then to locate the integration site more precisely. This further analysis would consist primarily of DNA hybridizations, subcloning, and sequencing. The information thus obtained would allow for the cloning of a corresponding DNA fragment from a plant not engineered with a heterologous avidin gene. (In this context, "corresponding" denotes a DNA fragment that hybridizes under stringent conditions to the fragment containing the avidin gene.) The cloned fragment can be used for high level expression of another gene of interest. This is accomplished by introducing the other gene into the plant chromosome, at a position and in an orientation corresponding to that of the heterologous avidin gene. The insertion site for the gene of interest would not necessarily have to be precisely the same as that of the avidin gene, but simply in near proximity. Integration of an expression vector constructed as described above, into the plant chromosome then would be accomplished via recombination between the cloned plant DNA fragment and the chromosome. Recombinants, where the gene of interest resides on the chromosome in a position corresponding to that of the highly expressed avidin gene likewise should express the gene at high levels.

EXAMPLE 1

Construction of an Expression Vector Containing the Avidin and Bar Genes

A gene optimized for expression of avidin protein in maize was generated by designing overlapping, complementary synthetic oligonucleotide sequences containing compatible restriction site termini, which then could be annealed and ligated to yield the final gene. The optimized DNA sequence was determined by reverse-translating the known amino acid sequence of the chicken avidin gene, see Gope et al., supra, and then generating a DNA sequence by using a codon bias table for maize, wherein the amino acid codons occurring with a higher frequency in native maize genes were employed and infrequently used or unused codons were avoided. See Murray et al., supra. Additionally, a DNA sequence encoding the barley alpha amylase peptide signal sequence—Rogers et al., supra—was generated, via the same approach, and then was ligated to the 5' terminus of the avidin gene, in such a way that normal cellular processing of the translated pre-avidin protein would accurately cleave the signal sequence yielding mature avidin protein. This signal sequence was included based on the prediction that higher levels of avidin expression could be obtained if newly synthesized avidin protein was targeted to the extracellular compartment. The resultant signal sequence/avidin segment was cloned, as a BamHI/EcoRI fragment, into the vector pGEM3Zf+, a product of Promega Corporation (Madison, Wis.), to generate plasmid pPHI5142. A BamHI/HpaI fragment containing the signal sequence/avidin region was isolated and cloned into a plasmid derived from pBlueScript SK+ as a backbone (Stratagene, La Jolla, Calif.). In this plasmid, the fragment of DNA including the signal sequence/avidin was inserted between the maize ubiquitin 5' region (which includes the promoter, the first exon and first intron) and the potato proteinase inhibitor II (PinII) transcription terminator region, all constructed as described above. The resultant plasmid is pPHI5168 (FIG. 1B).

EXAMPLE 2

Generation of Avidin-Expressing, Transgenic Plants

Callus tissue derived from immature embryos of Hi-II were used for particle bombardment-mediated transformation using a helium-powered particle acceleration device, P DS 1000, which is commercialized by Bio-Rad (Hercules, Calif.). The procedure outlined by Gorden-Kamm, et al., supra was used for transformation and to select plants resistant to bialaphos. Plants initially regenerated from selected embryogenic tissue are termed $T_0$. Subsequent generations are termed T1, T2, etc. Transgenic plants were either selfed or used as females in crosses with untransformed maize plants.

TABLE 1

| PURIFICATION OF AVIDIN | |
|---|---|
| AMOUNT OF SEEDS | 1000 g |
| mg Protein/g of seed | 23.4 |
| Percentage avidin in extracted protein | 1.0 |
| Total mg of avidin | 249 |
| mg of Avidin/g of seed | 0.25 |
| mg of purified Avidin/g of seed | 0.28 |
| Percent recovery | 100 |

Material shows 8.8% internal cleavage by protein sequencing; final product is 12.7 U/mg.

TABLE 2

BIOCHEMICAL CHARACTERIZATION OF AVIDIN

| BIOCHEMICAL PROPERTIES | SIGMA AVIDIN | CORN AVIDIN |
|---|---|---|
| Molecular Weight | 17,700 | 16,800 |
| Binding Stoichiometry | Binds one biotin per subunit | Binds one biotin per subunit |
| pI | 10 | 10 |
| Antigenic Similarity | Identical | Identical |
| Glycosylated | Yes | Yes |

TABLE 3

N-TERMINAL PROTEIN SEQUENCING DATA

| | SIGMA AVIDIN | CORN AVIDIN |
|---|---|---|
| 1 | Ala | Ala |
| 2 | Arg | Arg |
| 3 | Lys | Lys |
| 4 | (Cys) | (Cys) |
| 5 | Ser | Ser |
| 6 | Leu | Leu |
| 7 | Thr | Thr |
| 8 | Gly | Gly |
| 9 | Lys | Lys |
| 10 | Trp | Trp |
| 11 | Thr | Thr |
| 12 | Asn | Asn |
| 13 | Asp | Asp |
| 14 | Leu | Leu |
| 15 | Gly | Gly |
| 16 | Ser | Ser |
| 17 | (Asn*) | (Asn*) |
| 18 | Met | Met |
| 19 | Thr | Thr |
| 20 | Ile | Ile |
| 21 | Gly | Gly |

*This position is blocked, presumably due to glycosylation of the protein.

What is claimed is:

1. A transgenic plant stably transformed with a DNA molecule that comprises (i) a plant-compatible promoter, (ii) a signal sequence, and, (iii) a heterologous, avidin-encoding sequence that are operably linked, such that at least 0.1% of total extracted protein is avidin.

2. A transgenic plant according to claim 1, wherein said plant is a corn plant.

3. A transgenic plant according to claim 2, wherein said plant is of strain 70415, germplasm of which strain has been deposited under ATCC Accession No. 97328.

4. A transgenic plant according to claim 1, wherein said avidin-encoding sequence incorporates plant-preferred codons.

5. A transgenic plant according to claim 1, wherein said signal sequence is a peptide export sequence.

6. A transgenic plant according to claim 5, wherein said peptide export sequence is a barley alpha amylase peptide export sequence.

7. A transgenic plant according to claim 1, wherein said DNA molecule further comprises an intron sequence.

8. A transgenic plant according to claim 7, wherein said intron is an ubiquitin intron.

9. A transgenic plant according to claim 1, wherein said plant compatible promoters is the ubiquitin promoter.

10. A transgenic plant according to claim 1, wherein said total extracted protein is about 1% avidin.

11. Seed that is the product of a plant according to claim 1.

12. Seed that is the product of a plant according to claim 10.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 484 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGATCCCAAC  AATGGCCAAC  AAGCACCTGA  GCCTCTCCCT  CTTCCTCGTG  CTCCTCGGCC      60

TCTCCGCCTC  CCTCGCCAGC  GGCGCCAGGA  AGTGCTCCCT  CACCGGCAAG  TGGACCAATG     120

ACCTCGGCTC  CAACATGACC  ATCGGCGCCG  TGAACTCCAG  GGGCGAGTTC  ACCGGCACCT     180

ACATCACCGC  CGTGACCGCC  ACCTCCAACG  AGATCAAGGA  GTCCCCCTC   CACGGTACCC     240

AGAACACCAT  CAACAAGAGG  ACCCAGCCCA  CCTTCGGCTT  CACCGTGAAC  TGGAAGTTCT     300

CCGAGTCCAC  CACCGTGTTC  ACCGGCCAGT  GCTTCATCGA  CCGCAACGGC  AAGGAGGTGC     360

TCAAGACCAT  GTGGCTCCTG  AGGAGCTCCG  TGAATGACAT  CGGCGACGAC  TGGAAGGCCA     420

CCCGCGTGGG  CATCAACATC  TTCACCCGCC  TCCGCACCCA  GAAGGAGTGA  TAGTTAACGA     480

ATTC                                                                      484
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Ala  Arg  Lys  Cys  Ser  Leu  Thr  Gly  Lys  Trp  Thr  Asn  Asp  Leu  Gly  Ser
 1              5                        10                       15

Asn  Met  Thr  Ile  Gly
               20
```

( 2 ) INFORMATION FOR SEQ ID NO:3:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Ala  Arg  Lys  Cys  Ser  Leu  Thr  Gly  Lys  Trp  Thr  Asn  Asp  Leu  Gly  Ser
 1              5                        10                       15

Asn  Met  Thr  Ile  Gly
               20
```